(12) United States Patent
Dragisic

(10) Patent No.: US 6,536,437 B1
(45) Date of Patent: Mar. 25, 2003

(54) CUFFED NASAL AIRWAY AND ANESTHETIC WAND SYSTEM

(76) Inventor: Branislav M. Dragisic, 7849 Forest Hill Rd., Burr Ridge, IL (US) 60525

(*) Notice: Subject to any disclaimer, the term of this patent is extended or adjusted under 35 U.S.C. 154(b) by 0 days.

(21) Appl. No.: 09/430,430

(22) Filed: Oct. 29, 1999

(51) Int. Cl.$^7$ .............................................. A61M 15/08

(52) U.S. Cl. ............................... 128/207.18; 128/207.14

(58) Field of Search ....................... 128/200.24, 200.26, 128/207.14–207.18, 911, 912, DIG. 26, 206.29, 207.29; 604/101.03, 102.01

(56) References Cited

U.S. PATENT DOCUMENTS

| | | | |
|---|---|---|---|
| 2,208,633 A | | 7/1940 | Heidbrink |
| 3,881,479 A | | 5/1975 | Carden |
| 3,915,173 A | | 10/1975 | Brekke |
| 3,964,488 A | | 6/1976 | Ring et al. |
| 4,150,676 A | * | 4/1979 | Jackson ...................... 128/351 |
| 4,284,076 A | | 8/1981 | Hall |
| 4,289,128 A | | 9/1981 | Rusch |
| 4,363,323 A | | 12/1982 | Geiss |
| 4,405,308 A | * | 9/1983 | Jessup ........................ 604/200 |
| 4,449,522 A | * | 5/1984 | Baum ..................... 128/200.26 |
| 4,543,951 A | | 10/1985 | Phuc |
| 4,593,689 A | | 6/1986 | White |
| 4,633,864 A | | 1/1987 | Walsh |
| 4,655,214 A | * | 4/1987 | Linder .................... 128/207.18 |
| 4,819,619 A | | 4/1989 | Augustine et al. |
| 4,821,713 A | | 4/1989 | Bauman |
| 4,821,715 A | | 4/1989 | Downing |
| 4,949,716 A | | 8/1990 | Chenoweth |
| 5,024,220 A | | 6/1991 | Holmgreen et al. |
| 5,139,510 A | * | 8/1992 | Goldsmith, III et al. .... 606/196 |
| 5,311,864 A | * | 5/1994 | Huerta .................... 128/207.15 |
| 5,313,939 A | * | 5/1994 | Gonzalez ................ 128/200.14 |
| 5,318,517 A | * | 6/1994 | Reiman ................. 128/207.14 |
| 5,348,000 A | | 9/1994 | Teves |
| 5,443,063 A | * | 8/1995 | Greenberg ............. 128/207.15 |
| 5,443,064 A | * | 8/1995 | Theis et al. ............ 128/207.15 |
| 5,477,852 A | | 12/1995 | Landis et al. |
| 5,540,224 A | | 7/1996 | Buret et al. |
| 5,590,647 A | | 1/1997 | Nye |
| RE35,531 E | | 6/1997 | Callaghan et al. |
| 5,642,730 A | | 7/1997 | Baran |
| 5,653,229 A | * | 8/1997 | Greenberg ............. 128/207.15 |
| 5,664,567 A | | 9/1997 | Linder |
| 5,713,855 A | * | 2/1998 | Shippert ...................... 604/54 |
| 5,735,829 A | | 4/1998 | Cherian |
| 5,740,799 A | | 4/1998 | Nielsen |
| 5,743,258 A | | 4/1998 | Sato et al. |
| 5,765,558 A | | 6/1998 | Psaros et al. |
| 5,791,341 A | | 8/1998 | Bullard |
| 5,800,408 A | * | 9/1998 | Strauss et al. ............... 604/264 |

(List continued on next page.)

Primary Examiner—Aaron J. Lewis
Assistant Examiner—Teena Mitchell
(74) Attorney, Agent, or Firm—King & Jovanovic, PLC

(57) ABSTRACT

A nasal airway system.comprising a cuffed nasal airway and a nasal wand. The cuffed nasal airway includes a flexible tube, an inflatable cuff and a member for inflating the cuff. The flexible tube includes a first end and a second end, a length, and an opening extending from the first end to the second end. The length of the tube is such that upon insertion into a nasal cavity of a patient, the second end is in substantial alignment with a soft palate and a lateral pharyngeal wall of a patient. The inflatable cuff is associated with the second end of the tube. The inflating member inflates the cuff after alignment of the flexible tube in a patient to, in turn, provide a seal with the soft palate, the lateral pharyngeal wall, and the base of the tongue of the patient. The nasal wand includes a housing, a flexible wand and a fluid delivery member. The housing includes an inner chamber with a fluid. The flexible wand is substantially soft and substantially bendable, and, includes a plurality of openings along the length thereof. The fluid delivery member capable of delivering the fluid through the openings in the wand.

18 Claims, 3 Drawing Sheets

U.S. PATENT DOCUMENTS

| | | | | |
|---|---|---|---|---|
| 5,827,224 A | * | 10/1998 | Shippert | 604/104 |
| 5,865,176 A | * | 2/1999 | O'Neil | 128/207.15 |
| 5,976,072 A | * | 11/1999 | Greenberg | 600/120 |
| 6,079,413 A | * | 6/2000 | Baran | 128/200.23 |
| 6,098,617 A | * | 8/2000 | Connell | 128/200.26 |
| 6,148,818 A | * | 11/2000 | Pagan | 128/207.15 |
| 6,394,093 B1 | * | 5/2002 | Lethi | 128/207.13 |
| 6,413,499 B1 | * | 7/2002 | Clay | 424/450 |

* cited by examiner

CUFFED NASAL AIRWAY AND ANESTHETIC WAND SYSTEM

BACKGROUND OF THE INVENTION

1. Field of the Invention

The present invention is directed to the establishment of airways in patients, and more particularly to a system to provide a cuffed nasal airway and anesthetic wand.

2. Background Art

Devices for providing airways for patients have long been known in the art. Generally, the devices are inserted deep into the throat of the user, thereby disrupting the vocal chords and other structures. Although such devices are required in certain instances, there has been a need to adopt less invasive procedures and apparatuses for certain applications.

Generally, such less invasive structures comprise structures such as Sato et al, U.S. Pat. No. 5,743,258, among others. Such structures, while not as invasive as conventional airways nevertheless are quite intrusive. Such structures are inserted generally through the mouth of the patient. As a result, the patient must keep his/her mouth open. In addition, these devices are often made from rigid materials that can cause damage to teeth (i.e., chipped or broken teeth) as well as dental work. Further, these devices are difficult to position within the mouth since they are smaller than the oral cavity, and therefore require frequent repositioning.

Certain other devices have been adopted for use and application through the nose. These include Brekke, U.S. Pat. No. 3,915,173 and Bullard, U.S. Pat. No. 5,791,341. While these devices utilize the nasal passageway, the devices suffer from other drawbacks. For example, the Brekke '173 reference discloses a device that is highly invasive. Additionally, the Bullard '341 reference discloses a device which is cumbersome, difficult to position properly, and rather invasive. In addition, the complex structure is relatively expensive to produce.

Accordingly, it is an object of the invention to provide a device which can provide a cuffed nasal airway.

It is an additional object of the invention to provide a minimally invasive airway for a patient.

It is a further object of the invention to provide a means for applying an anesthetic to the nasal passage.

It is a further object of the invention to overcome the aforementioned limitations of the prior art.

These and other objects will become apparent in light of the specification, drawings and claims appended hereto.

SUMMARY OF THE INVENTION

The invention comprises a nasal airway system which comprises a cuffed nasal airway and a nasal wand.

The cuffed nasal airway includes a flexible tube, an inflatable cuff and a member for inflating the cuff. The flexible tube includes a first end and a second end, a length, and an opening extending from the first end to the second end. The length of the tube is such that upon insertion into a nasal cavity of a patient, the second end is in substantial alignment with the base of the tongue, soft palate and lateral pharyngeal wall of a patient. The inflatable cuff is associated with the second end of the tube. The inflating member inflates the cuff after alignment of the flexible tube in a patient to, in turn, provide a seal with the soft palate, the lateral pharyngeal wall, and the base of the tongue of the patient.

In a preferred embodiment, the cuff includes a proximal end and a distal end, the distal end of the cuff corresponding to the second end of the flexible tube.

In another preferred embodiment, the first end of the tube includes a coupling to facilitate connection to an outside device. In one embodiment, the coupling comprises a diameter of 15 mm. In another such embodiment, the coupling includes a handle region which facilitates coupling to an outside device.

In yet another embodiment, the tube includes at least one reinforcement member. The reinforcement member facilitating the flexing of the tube relative to itself beyond ninety degrees without collapsing the tube. In a preferred embodiment, the reinforcement member comprises a plurality of ribs positioned along at least a portion of the tube from the first end to the second end. In another preferred embodiment, the ribs comprise a metal embedded within the tube.

In another preferred embodiment, the first end of the tube includes a stopper slidably positionable along the tube to preclude inadvertent movement of the cuffed nasal airway after insertion and alignment of same.

The nasal wand includes a housing, a flexible wand and a fluid delivery member. The housing includes an inner chamber with a fluid. The flexible wand is substantially soft and substantially bendable, and, includes a plurality of openings along the length thereof. The fluid delivery member capable of delivering the fluid through the openings in the wand.

In a preferred embodiment, the housing includes at least one plunger slidably movable within the inner chamber.

In another embodiment, the flexible wand includes a plurality of openings extending in a radial pattern.

In yet another embodiment, the flexible wand includes means for precluding trauma to the nasal tissue.

DETAILED DESCRIPTION OF THE DRAWINGS

Figure 1:
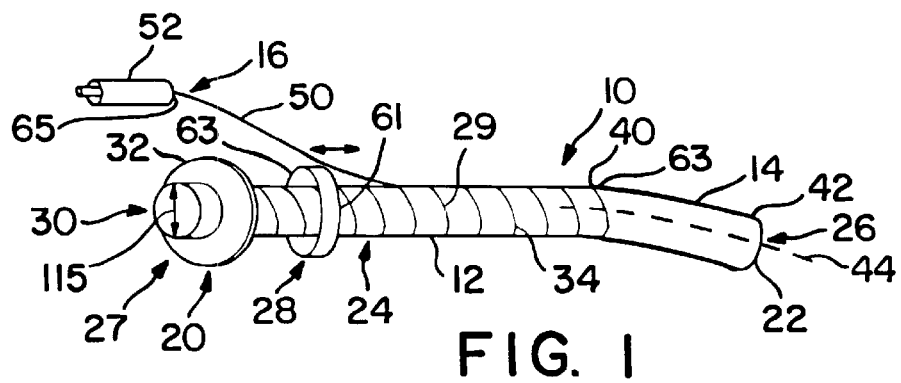
FIG. 1 of the drawings is a perspective view of a cuffed nasal airway of the present invention shown with a deflated cuff.
Figure 2:
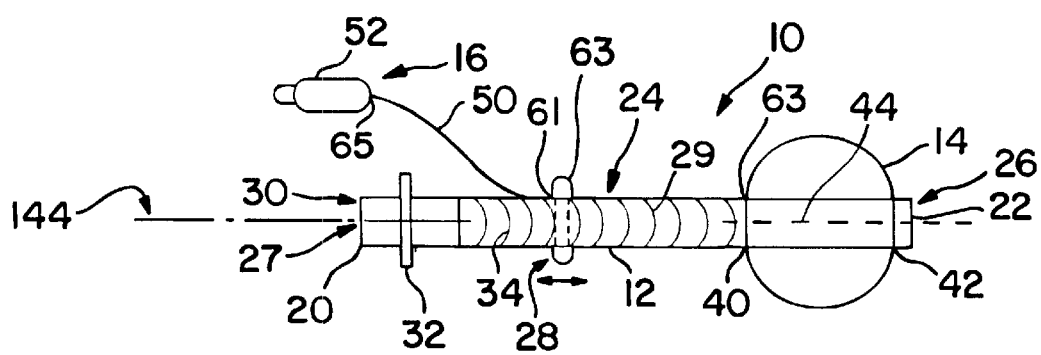
FIG. 2 of the drawings is a side elevational view of the cuffed nasal airway shown with an inflated cuff.

While this invention is susceptible to embodiment in many different forms, there is shown in the drawings and will be described below in detail, specific embodiments with the understanding that the embodiment is to be considered to be an exemplification of the principles of the invention, and the embodiment is not intended to limit the invention to the embodiment illustrated.

Cuffed nasal airway 10 is shown in FIGS. 1–4 as comprising flexible tube 12, inflatable cuff 14, and means 16 for inflating the cuff. As will be explained, cuffed nasal airway 10 is inserted into patient's nasal passage and positioned so that when the cuff is inflated, it effectively seals the airway by sealing against the soft palate, the lateral pharyngeal wall, and the base of the tongue of the patient. In addition, airway 10 provides the seal with no invasion into the vocal cords or tracheal area, and, by insertion through the nose, with no susceptibility to dental damage and/or inadvertent dislodging, even if the patient's movement is not restrained.

Flexible tube 12, as shown in FIGS. 1–4, comprises first end 20, second end 22, length 24, opening 26 extending from first end 20 to second end 22, connection coupling 27, stopper 28, and means 29 for reinforcement of the tube. Length 24 is such that, upon insertion into a patient's nose, inflatable cuff 14 is in substantial alignment with the soft palate and the lateral pharyngeal wall of the patient. Opening 26 provides a useable airway once sealing contact has been established by inflatable cuff 14. First end 20, second end 22, and opening 26 all have substantially similar diameters. The diameter is sufficient to provide for unimpeded airflow. To facilitate insertion and usage in the nose and throat, tube 12 is constructed of flexible and moisture-resistant material, such as a plastic which is latex-free. In addition, such a plastic is capable of being sterilized and packaged in a single use packaging. Of course, tubing which can be autoclaved is likewise contemplated for use.

As shown in FIGS. 1–4, connection coupling 28 is associated with first end 20, and facilitates attachment of the tube 12 to an outside device such as an ambulatory bag or the like. Connection coupling 28 may consist of cylindrical opening 30 with a diameter of 15 mm (denoted by the reference number 115 at FIG. 2), and may include a handle region 32 which facilitates handling by the physician or his/her assistants. Of course, the connection coupling may take on various shapes and dimensions. The opening shown having a diameter of 15 mm is a universally accepted coupling and such a coupling is commonly utilized in association with outside medical devices. In addition, connection coupling may include structures which receive the ends of a head strap to facilitate the retained positioning of the cuffed nasal airway. However, due to the relatively snug fit of the tube within the nasal passage, it will be understood that even without any head strap, the device is substantially restrained and precluded from movement.

Reinforcement means 29 facilitate flexing tube 12 relative to itself beyond ninety degrees without collapsing tube 12 so that it may be positioned in the nasal passageway without the possibility of collapse. Reinforcement means 29 comprises, for example, a plurality of circular ribs 34 positioned along at least a portion of tube 12 from first end 20 to second end 22. Ribs 34 consist of a rigid or semi-rigid material, such as metal, that is embedded into tube 12. Of course, other means of reinforcing the flexible tube are likewise contemplated for use, such as the selection of a tube material which facilitates bending of the tube but precludes the collapse of the tubing or the use of other rigidifying structures.

Stopper 28, which is slidably positioned near first end 20 of flexible tube 12, includes inner surface 61 and receipt region 63. Inner surface 61 of stopper 28 is in abutting engagement with the outer surface of the flexible tube and facilitates slidable positioning of the stopper along substantially the entire length of the flexible tube. Inner surface 61 is configured so as to provide a certain amount of resistance to movement along the flexible tube. In this manner, after insertion of tube 12 and after stopper 28 is slidably positioned so as to rest against the patient's nose, stopper 28 will tend to remain in the desired position and will not inadvertently slide along the flexible tube into another position until positively and intentionally repositioned by the user.

Inflatable cuff 14 comprises proximal end 40, distal end 42, and axis 44. Inflatable cuff is associated with second end 22 of tube 12, and is positioned so that distal end 42 substantially corresponds with second end 22 of flexible tube 12. Axis 44, running through the center of the inflatable cuff 14, substantially corresponds to the longitudinal axis 144 of tube 12 although such positioning is not critical so long as the configuration permits effective sealing after inflation of the cuff. The cuff is dimensional so as to be capable of inflation to seal the cavity of a patient between the base of the tongue, the soft palate and the lateral pharyngeal wall. Inflatable cuff 14 comprises a relatively pliable material which is capable of high volume/low pressure inflation. Further, when evacuated of any air, the inflatable cuff lies substantially flat against the tube and does not significantly add to the overall thickness of the tube. In turn, it does not inhibit insertion of the tube into the nose of the user.

Figure 3:
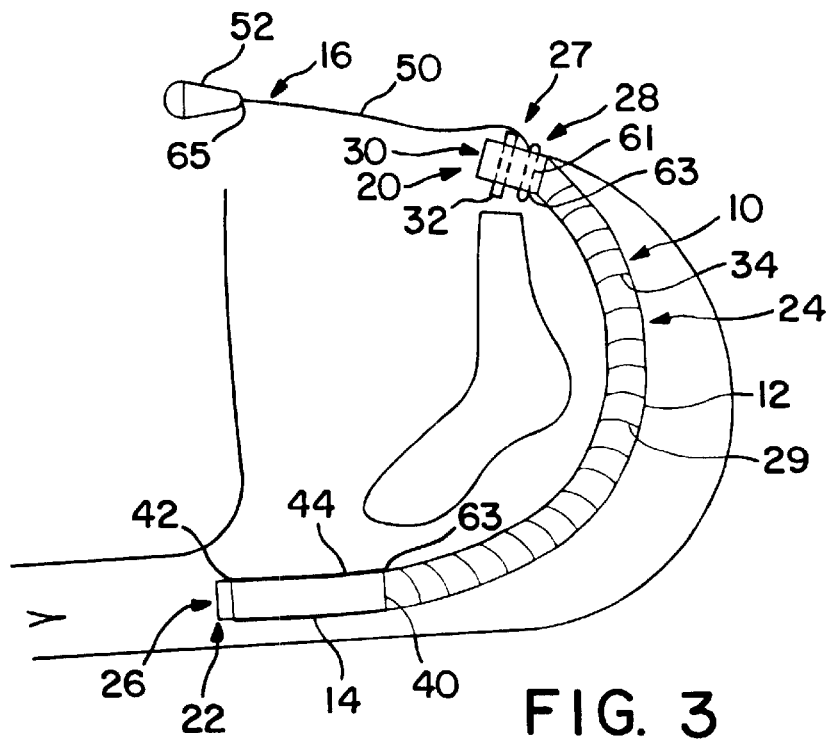
FIG. 3 of the drawings is a side elevational view of the inserted cuffed nasal airway with a deflated cuff.
Figure 4:
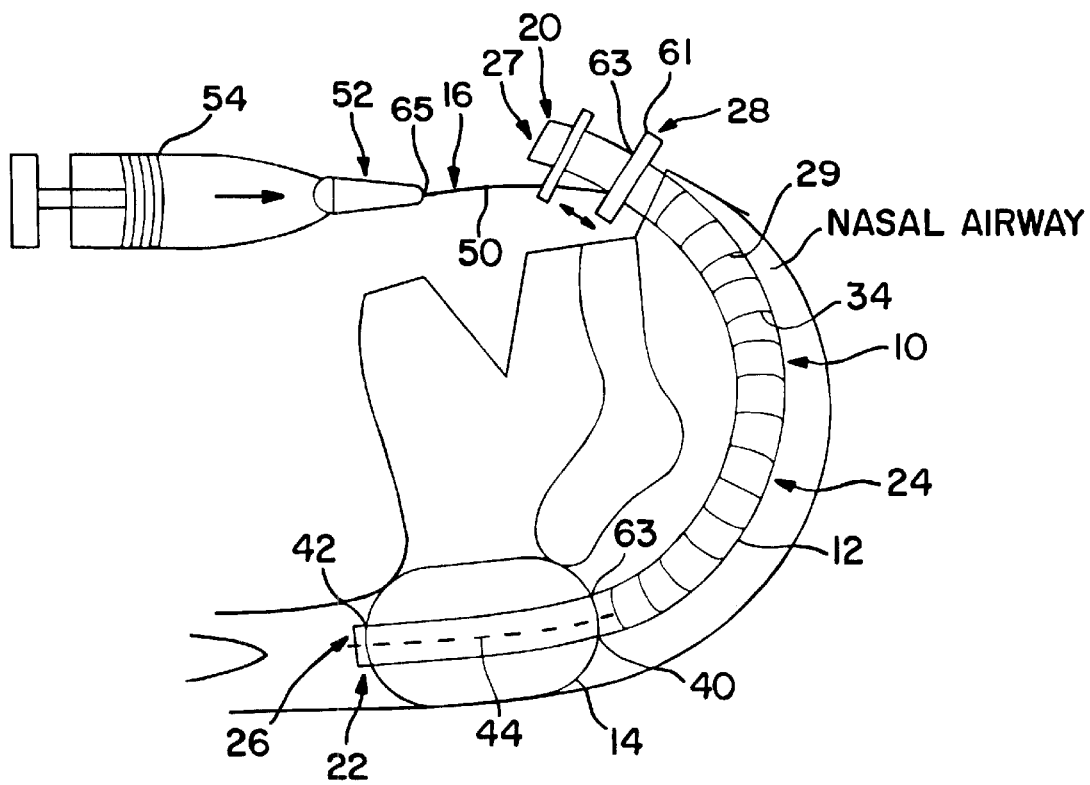
FIG. 4 of the drawings is a side elevational view of the inserted cuffed nasal airway with an inflated cuff.
Figure 5:
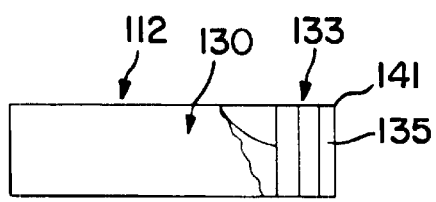
FIG. 5 of the drawings is a side elevational view of a fluid filled nasal wand fluid housing.

As shown in FIGS. 1–4, inflation means 16 comprises hose 50, valve 52, and inflation device 54 (FIG. 4). Hose 50 includes a first end 63 which is in fluid communication with inflatable cuff 14, and a second end 65 extending from cuff 14 toward first end 20. Hose 50 may be separated from flexible tube 12 or, alternatively, hose 50 may be embedded in tube 12 or co-molded with tube 12. Second end 65 of hose 50 is associated with valve 52 to regulate the flow of air into and out of cuff 14. Valve 52 facilitates the flow of air into or out of cuff 14 when connected with inflation device 54, and prevents the flow of air into or out of cuff 14 when not connected. Inflation device 54 can consist of any forced-air device, for example, a needleless syringe, a pump or other such suitable structure.

Figure 6:
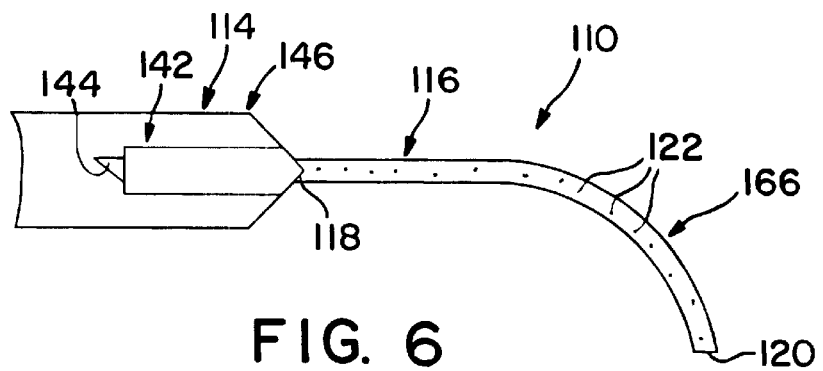
FIG. 6 of the drawings is a side elevational view of a nasal wand without the fluid filled housing.
Figure 7:
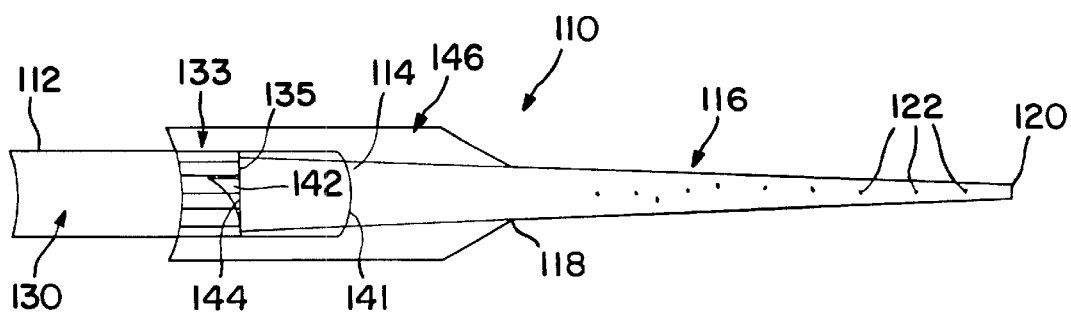
FIG. 7 of the drawings is a side elevational view of the nasal wand with a fluid filled housing.
Figure 8:
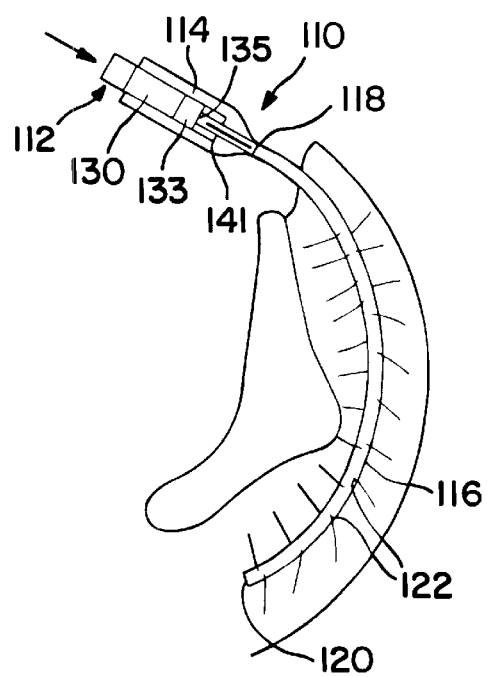
FIG. 8 of the drawings is a side elevational view of the inserted nasal wand.

Nasal wand 110 is shown in FIGS. 6–8 as comprising fluid housing 112, means 114 for delivering the fluid and flexible wand 116. Fluid housing 112 comprises inner chamber 130, plunger 133 and frangible opening 135. Inner chamber includes open end 141 and is capable of receiving a predetermined quantity of a medicament such as a topical anesthetic (i.e., 80 mg (40 mg/ml) 2 mL lidocaine+sodium hydroxide–ph 5.0–7.0) with a vasoconstrictor (neo-synephryne 0.5% ½ ml). Fluid housing 112 may comprise a rigid plastic material or a glass material. Preferably, the housing is a substantially cylindrical, graduated and transparent or translucent container. As such, the physician can determine the quantity of fluid that has been dispensed as well as the quantity of fluid which remains in the housing. Plunger 133 is positioned to interface and seal open and 141, and plunger is dimensioned so as to facilitate sealed slidable movement of the plunger within the inner chamber in a piston/cylinder configuration. Plunger 133 is preferably a rubberized material or a silicone material which is readily capable of providing sealed engagement with the fluid housing. Frangible opening 135 is associated with the plunger 133. As will be explained, fluid delivery means 114 includes means for piercing frangible opening 135.

Specifically, fluid delivery means 114 includes plunger coupling 142, piercing means 144 and means 146 for receiving housing 112. Plunger coupling 142 comprises a member which is configured to retain plunger 133 while permitting slidable movement thereof. Piercing means 144 is configured so as to pierce frangible opening 135 upon placement of housing 112 and plunger 133 on plunger coupling 142. The receiving means facilitates the receipt of the housing as plunger 133 is slidably directed through the inner chamber of the housing.

Figure 9:
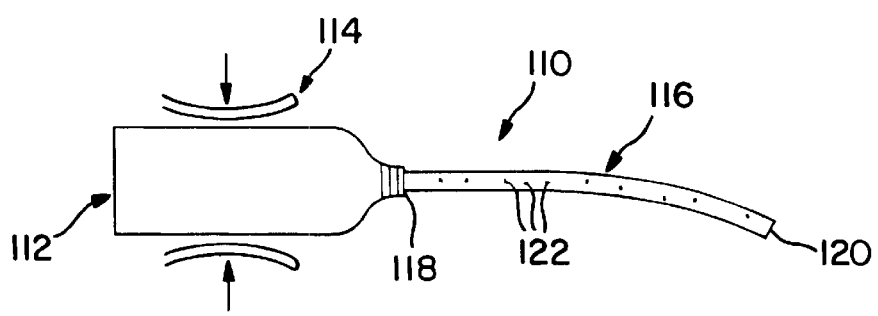
FIG. 9 of the drawings is an alternate embodiment of the nasal wand of the present invention.

In another embodiment, the fluid delivery means and the fluid housing may comprise a flexible container which, upon compression, forces fluid from an opening in the container. Such an embodiment is shown in FIG. 9. Indeed, the particular fluid delivery means is not limited to the embodiments shown and, in turn, any fluid delivery means which can accurately deliver fluid to the flexible wand in sufficient quantities may be utilized with the present invention.

Flexible wand 116 is shown in FIGS. 6–9 as comprising first end 118, second end 120 and openings 122. First end 118 is in fluid communication with plunger coupling. As a result, as the plunger is directed through inner chamber 130, fluid is directed to plunger coupling and, in turn, through first end 118 of flexible wand 116. Second end 120 is spaced apart from first end 118, thereby defining a length for the flexible wand.

Generally, the flexible wand is dimensioned so that it may be inserted into the nose of the patient to the base of the tongue. Openings 122 are positioned at predetermined positions along the entire length of flexible wand 116. As a result, as the fluid extends through the flexible wand, the fluid exits radially through openings 122. The openings are positioned so as to facilitate the distribution of fluid uniformly in all directions. Of course, the precise distribution of fluid can be determined through experimentation.

The flexible wand comprises a material such as silicone which is infinitely flexible and bendable to follow the contours of the nasal passageway. Since the flexible wand carries the anesthetic, and prior to insertion, the nasal passage does not generally have any anesthetic applied thereto, if the wand is not suitably flexible and/or soft, damage or trauma may occur in the nasal passage. The flexibility thereof provides a means 166 for precluding trauma to the nasal passageway. The currently available tubes with radially extending openings along the length thereof have some degree of flexibility, but the material hardness and the limited flexibility would not facilitate use in the nasal passageway.

In operation, the cuffed nasal airway 10 and wand 110 is used by the anesthesiologist, ER physician, oral surgeon or other physicians to ultimately provide a path for air to flow to facilitate breathing while enabling constant and unimpeded access to the mouth, enhancing comfort, minimizing injury and trauma to the patient (i.e. dental damage) while minimizing the invasiveness of the airway.

To utilize the system, the physician first prepares wand 110. Specifically, fluid housing 112 is selected which includes an acceptable quantity of a suitable topical anesthetic with a vasoconstrictor fluid. Once selected, housing 112 is attached to fluid delivery means 114 so that plunger 133 is coupled with plunger coupling 142. As the two are coupled, piercing means 144 pierces frangible opening 135.

Next, as shown in FIG. 8, the physician inserts flexible wand 116 into the patient's nasal passage. Due to the softness and flexibility of the wand, the wand is easily insertable and precludes trauma to the patient. Once inserted and properly positioned, housing 112 is slidably moved relative to the fluid delivery means 114 so as to force plunger 133 through inner chamber 130. This movement of the plunger forces the topical anesthetic from within the inner chamber through frangible opening 135. Once forced through the frangible opening, the fluid proceeds into flexible wand 116 and is ejected through openings 122 into the nasal passage of the patient. By moving the plunger at a predetermined rate, a suitable fluid flow can be created and maintained so as to facilitate a suitable fluid spray through the openings.

Once the desired amount of fluid has been sprayed into the nasal passage, the nasal wand 110 is removed from the patient. Of course, should large quantities of anesthetic be required, a second or third fluid housing can be utilized. In particular, once a fluid housing is emptied, the fluid housing can be removed from delivery means 114 and a new fluid housing can be utilized. This procedure can be repeated until the required dose of anesthetic is delivered to the nasal passage.

Once the anesthetic has taken effect, the nasal cavity is prepared with a lubricant preferably an anesthetic lubricant (lidocaine or benzocaine) to provide for the easy insertion of the airway 10. As shown in FIG. 3, the second end 22 of the airway 10 is then inserted into the nasal cavity, and positioned so the second end, and specifically the inflatable cuff 14 is aligned with the soft palate, the lateral pharyngeal wall, and the base of the tongue of the patient. The length 24 of the tube 12 is such that, once aligned, the tube 12 is not invasive into the vocal cords or the tracheal area—and in effect the second end of the tube is spaced apart from these structures and does not affect these structures.

After alignment, stopper 28 is slidably moved along flexible tube 12 until it abuts the outer edge of the nostril. While an embodiment may be utilized without a stopper, the stopper further serves to secure the tube 12 in desired position, and precludes inadvertent movement of the tube.

Once fully positioned, as shown in FIG. 4, inflation device 54 is connected to valve 52 of inflation means 16. Inflation means is then used to inflate cuff 14 to a sufficient size so as to provide sealing contact with the soft palate, lateral pharyngeal wall, and base of the tongue of the patient. Once sealing contact is achieved, an outside device may be connected to the connection coupling 28 to provide intubating gasses to the patient through the opening 26. If necessary, a separate tube 12 can be inserted into each nostril. In such a situation, the two cooperate to isolate the desired airway and provide enhanced airflow.

The system comprising the wand and the cuffed nasal airway can be utilized together to facilitate the establishment of a minimally invasive airway. In particular, such devices are useful with patients that are restless or difficult to control, inasmuch as the nasal passage is substantially smaller than the oral passage. Thus, while it is difficult to control airways in the oral cavity, control of the present invention in the nasal cavity is rather easily accomplished. Moreover, the use of a nasal passage minimizes discomfort to the patient. Indeed, the establishment of an oral passageway requires that the user retain his/her mouth open for an extended period of time. Further still, the use of airways in the oral cavity can lead to dental problems such as chipped teeth, broken dental work among others. The use of the invention eliminates the dental problems associated with the establishment of an airway for the patient.

The foregoing description and drawings merely explain and illustrate the invention, and the invention is not limited thereto, as those skilled in the art who have the disclosure before them will be able to make modifications and variations to the system without departing from the scope of the invention.

What is claimed is:

1. A cuffed nasal airway comprising:

a flexible tube having a first end and a second end, a length, and an opening extending from the first end to the second end, the length of the flexible tube being such that upon insertion into a nasal cavity of a patient, the second end is in substantial alignment with a soft palate and a lateral pharyngeal wall of a patient;

an inflatable cuff positioned at the second end of the tube;

means for inflating the cuff after alignment of the flexible tube in a patient to, in turn, provide a seal with the soft palate, the lateral pharyngeal wall, and a tongue of a patient.

2. The airway of claim 1 wherein the cuff includes a proximal end and a distal end, the distal end of the cuff corresponding to the second end of the flexible tube.

3. The airway of claim 1 wherein the first end of the flexible tube includes a coupling to facilitate connection to an outside device.

4. The airway of claim 3 wherein the coupling comprises an opening having a diameter of 15 mm.

5. The airway of claim 3 wherein the coupling includes a handle region which facilitates connection of the coupling to an outside device.

6. The airway of claim 1 where the flexible tube includes at least one reinforcement member, facilitating flexing the tube relative to itself ninety degrees without collapsing the tube.

7. The airway of claim 6 wherein the reinforcement member comprises a plurality of ribs positioned along at least a portion of the flexible tube from the first end to the second end.

8. The airway of claim 7 wherein the ribs are made of metal, and, at least a portion of which is embedded within the flexible tube.

9. The airway of claim 1 where the first end of the flexible tube includes a stopper slidably positionable along the tube to, in turn, further preclude inadvertent movement of the cuffed nasal airway after insertion and alignment relative to the patient.

10. The airway of claim 1 where the inflation means comprises a hose extended from the cuff toward the first end of the flexible tube.

11. The airway of claim 10 where at least a part of the hose is embedded into the flexible tube.

12. The airway of claim 10 wherein the hose includes a valve which provides selective passage of air therethrough.

13. The airway of claim 1 wherein the cuff has an axis which corresponds to a longitudinal axis of the flexible tube.

14. The airway of claim 1 wherein the flexible tube comprises a substantially flexible plastic material.

15. The airway of claim 1 wherein the cuff comprises a substantially rigid plastic material.

16. A nasal airway system comprising:

a cuffed nasal airway including:

a flexible tube having a first end and a second end, a length, and an opening extending from the first end to the second end, the length of the tube being such that upon insertion into a nasal cavity of a patient, the second end is in substantial alignment with a soft palate and a lateral pharyngeal wall of a patient;

an inflatable cuff positioned at the second end of the flexible tube;

means for inflating the cuff after alignment of the flexible tube in a patient to, in turn, provide a seal with the soft palate, the lateral pharyngeal wall, and a tongue of a patient; and;

a nasal wand including:

a housing having an inner chamber with a fluid;

a flexible wand being substantially soft and substantially bendable, to, in turn, facilitate the insertion thereof through a nasal passage of a patient substantially without adversely affecting soft tissue of a nasal passage of a patient, the flexible wand having a plurality of openings along the length thereof; and means for delivering the fluid through the openings in the wand.

17. A method of nasal intubation comprising the steps of:

providing a nasal wand having a plurality of openings therethrough, the nasal wand being substantially soft and substantially bendable, to, in turn, facilitate the insertion thereof through a nasal passage of a patient substantially without adversely affecting soft tissue of a nasal passage of a patient;

inserting the nasal wand into the nasal passage of a patient;

delivering a topical anesthetic through at least some of the plurality of openings in the nasal wand;

removing the nasal wand from the nasal passage of a patient;

providing a cuffed nasal airway having a flexible tube and an inflatable cuff positioned at a second end thereof;

inserting the second end of the flexible tube through the nasal passage of a patient;

positioning the second end of the flexible tube with the soft palate and lateral pharyngeal wall of a patient;

inflating the inflatable cuff; and contacting at least a portion of the soft palate, the lateral pharyngeal wall and a tongue of a patient to, in turn, form a substantial seal with the inflatable cuff.

18. The method of claim 17 further comprising the step of applying a lubricant to the nasal passage to provide for easy insertion of the cuffed nasal airway.

* * * * *